United States Patent
Kudaravalli et al.

(10) Patent No.: US 9,889,269 B2
(45) Date of Patent: Feb. 13, 2018

(54) SYSTEMS AND METHODS FOR GENERATING LIQUID OXYGEN FOR PORTABLE USE

(75) Inventors: Ravikumar V. Kudaravalli, Manassas, VA (US); Michael Shin, Pleasanton, CA (US)

(73) Assignee: Caire Inc., Ball Ground, GA (US)

( * ) Notice: Subject to any disclaimer, the term of this patent is extended or adjusted under 35 U.S.C. 154(b) by 369 days.

(21) Appl. No.: 13/120,444

(22) PCT Filed: Aug. 28, 2009
(Under 37 CFR 1.47)

(86) PCT No.: PCT/US2009/055277
§ 371 (c)(1),
(2), (4) Date: Nov. 11, 2011

(87) PCT Pub. No.: WO2010/039369
PCT Pub. Date: Apr. 8, 2010

(65) Prior Publication Data
US 2013/0068220 A1    Mar. 21, 2013

Related U.S. Application Data

(60) Provisional application No. 61/099,390, filed on Sep. 23, 2008.

(51) Int. Cl.
*F25J 1/00*     (2006.01)
*A61M 16/10*    (2006.01)
(Continued)

(52) U.S. Cl.
CPC .... *A61M 16/1075* (2013.01); *A61M 16/0057* (2013.01); *F25J 3/044* (2013.01);
(Continued)

(58) Field of Classification Search
CPC .... F25J 3/04981; F25J 3/04169; F25J 1/0027; F25J 1/0017; F25J 2270/02; F17C 2270/02
(Continued)

(56) References Cited

U.S. PATENT DOCUMENTS 3,108,825 A * 10/1963 MacDonald, Jr. ...... F16L 19/00
                                                     285/148.19
4,017,284 A    4/1977 Gifford
(Continued)

FOREIGN PATENT DOCUMENTS

DE       19961230 A1    7/2001
JP       2003-515086 A  4/2003
(Continued)

OTHER PUBLICATIONS

PCT International Search Report and Written Opinion dated Jul. 25, 2012, for corresponding PCT application No. PCT/US2009/055277.

*Primary Examiner* — Frantz Jules
*Assistant Examiner* — Brian King
(74) *Attorney, Agent, or Firm* — Mintz Levin Cohn Ferris Glovsky and Popeo, P.C.

(57) ABSTRACT

A system for generating liquid oxygen (LOX) for portable use by a patient includes a patient portable unit configured to store LOX and deliver gaseous oxygen (GOX) to the patient, and a mobile base unit configured to generate LOX
(Continued)

by cryogenic separation of air and deliver the generated LOX to the patient portable unit. The mobile base unit includes a compressor that receives and pressurizes air, a purifier that removes impurities from the pressurized air, a heat exchanger that cools the purified air, a cryocooler that further cools the air to cryogenic temperatures, and a distillation unit that separates the cryogenic air into multiple products, including LOX and one or more cold byproducts. The separated LOX is communicated toward storage, and at least one of the cold byproducts is passed through the heat exchanger to facilitate heat transfer from incoming purified air to the at least one cold byproduct in order to cool the purified air.

8 Claims, 7 Drawing Sheets

(51) Int. Cl.
*F25J 3/04* (2006.01)
*A61M 16/00* (2006.01)

(52) U.S. Cl.
CPC ....... *F25J 3/04278* (2013.01); *F25J 3/04981* (2013.01); *F25J 2200/72* (2013.01); *F25J 2205/24* (2013.01); *F25J 2215/50* (2013.01); *F25J 2270/90* (2013.01)

(58) Field of Classification Search
USPC ........................... 62/640, 643, 648, 652, 656
See application file for complete search history.

(56) References Cited

U.S. PATENT DOCUMENTS

| | | | |
|---|---|---|---|
| 5,779,768 A * | 7/1998 | Anand | B01D 53/002 95/105 |
| 5,893,275 A | 4/1999 | Henry | 62/615 |
| 5,979,440 A * | 11/1999 | Honkonen | B01D 5/0039 128/200.24 |
| 6,212,904 B1 | 4/2001 | Arkharov et al. | 62/615 |
| 6,698,423 B1 | 3/2004 | Honkonen et al. | 128/201.21 |
| RE43,398 E * | 5/2012 | Honkonen | B01D 5/0039 128/200.24 |
| 2004/0045315 A1* | 3/2004 | Kamoshita | F25B 9/145 62/615 |
| 2004/0118285 A1* | 6/2004 | Kim et al. | 96/55 |
| 2005/0121303 A1* | 6/2005 | de Graauw | B01D 3/14 203/2 |
| 2005/0247308 A1* | 11/2005 | Frye et al. | 128/200.24 |
| 2005/0274142 A1* | 12/2005 | Corey | F25J 3/04278 62/643 |
| 2006/0260358 A1* | 11/2006 | Kun | F25J 3/04242 62/643 |
| 2007/0039616 A1* | 2/2007 | Hughes | F17C 6/00 128/201.21 |
| 2008/0042382 A1* | 2/2008 | Dodier et al. | 280/47.26 |

FOREIGN PATENT DOCUMENTS

| | | |
|---|---|---|
| WO | WO-90/08932 A1 | 8/1990 |
| WO | WO-01/36862 A1 | 5/2001 |

* cited by examiner

SYSTEMS AND METHODS FOR GENERATING LIQUID OXYGEN FOR PORTABLE USE

CROSS-REFERENCE TO RELATED APPLICATIONS

This application is a U.S. National Stage Application of International Application No. PCT/US2009/055277 filed Aug. 28, 2009, which designates the United States of America, and claims priority to U.S. Provisional Application No. 61/099,390 filed Sep. 23, 2008. The contents of which are hereby incorporated by reference in their entirety.

TECHNICAL FIELD

The present disclosure relates generally to the field of medical devices, e.g., systems and methods for generating liquid oxygen for portable use.

BACKGROUND

Therapeutic oxygen is commonly provided to subjects in order to treat a variety of medical conditions, including various conditions in which the subject suffers from a loss of lung capacity. Examples of medical conditions that may result in a loss of lung capacity include chronic obstructive pulmonary disease (COPD) such as asthma, emphysema, etc., as well as cystic fibrosis, lung cancer, lung injuries, and cardiovascular diseases. Pure or substantially pure oxygen may be delivered to the subject to treat the relevant condition. Inhaling the delivered therapeutic oxygen may help the subject achieve and/or maintain an adequate level of oxygen in his or her bloodstream.

Portable therapeutic oxygen has conventionally been provided in two ways. The first approach involves storing compressed oxygen gas in a pressure container and delivering the gas through a pressure regulator and through a hose, lumen, cannula or other passage to the subject's breathing orifices (e.g., nostrils). In some instances, the container may be wheeled such that the subject may be at least somewhat mobile. However, portable compressed gaseous oxygen systems suffer from various disadvantages, such as the fact that a full portable container typically lasts a relatively short period of time, and the fact that the system may be relatively heavy and obtrusive, which may limit the subject's mobility.

The second approach involves storing liquid oxygen (or "LOX") in a portable container and delivering gaseous oxygen evaporated from the liquid oxygen to the subject through a hose, lumen, cannula or other passage to the subject's breathing orifices (e.g., nostrils). Such an apparatus for storing liquid oxygen and/or delivering evaporated gaseous oxygen may be referred to as an "LOX apparatus." Although oxygen is typically a gas at standard atmospheric conditions, it may be maintained as a liquid at very low temperatures, which substantially reduces the volume of the oxygen, thus substantially reducing the required size of the LOX apparatus as compared to compressed gaseous oxygen systems. LOX apparatuses typically include a vacuum-insulated container with multilayer radiation insulation for storing and maintaining the LOX at a very low temperature.

As compared to compressed gaseous oxygen systems, an LOX apparatus enjoys a longer usable charge for a given size or weight. Accordingly, the LOX apparatus can be much smaller than known compressed gaseous oxygen systems and can provide the same or longer duration of useable charge, while being lighter and/or less obtrusive. However, typical existing LOX systems include a portable LOX container that must be refilled from a liquid oxygen dewars, which must be refilled or replaced regularly (e.g., once a month), typically by truck delivery.

SUMMARY

In accordance with one embodiment of the present disclosure, a system for generating liquid oxygen (LOX) for portable use by a patient includes a patient portable unit configured to store LOX and deliver gaseous oxygen (GOX) to the patient, and a mobile base unit configured to generate LOX by cryogenic separation of air and deliver the generated LOX to the patient portable unit. The mobile base unit includes a compressor configured to receive air and pressurize the air; a purifier configured to remove impurities from the pressurized air; a recuperative heat exchanger configured to cool the purified air; a cryocooler configured to receive cooled air from the recuperative heat exchanger and further cool the air to cryogenic temperatures; and a distillation unit configured to separate the cryogenic air into multiple products, including LOX and one or more byproducts, communicate the LOX toward storage; and communicate at least one byproduct toward the recuperative heat exchanger as at least one cold byproduct flow. The recuperative heat exchanger is configured to cool the purified air by transferring heat from the purified air to the at least one cold byproduct flow.

In accordance with another embodiment of the present disclosure, a system is provided for generating liquid oxygen (LOX) by cryogenic separation of oxygen from air for use in a patient portable reservoir configured to deliver gaseous oxygen (GOX) to the patient and configured to be portable with the patient. The system includes a compressor configured to receive air and pressurize the air; a purifier configured to remove impurities from the pressurized air; a recuperative heat exchanger configured to cool the purified air; a cryocooler configured to receive cooled air from the recuperative heat exchanger and further cool the air to cryogenic temperatures; and a distillation unit configured to separate the cryogenic air into multiple products, including LOX and one or more byproducts, communicate the LOX for transfer to the patient portable reservoir, and communicate at least one byproduct toward the recuperative heat exchanger as at least one cold byproduct flow. The recuperative heat exchanger is configured to cool the purified air by transferring heat from the purified air to the at least one cold byproduct flow.

In accordance with another embodiment of the present disclosure, a method for generating liquid oxygen (LOX) for use in a portable unit by cryogenic separation of oxygen from air is provided. The method includes communicating air through a compressor to increase the pressure of the air; communicating the pressurized air through a multiple column purifier to remove impurities from the pressurized air; communicating the purified air through a recuperative heat exchanger to cool the purified air; communicating the cooled air to a cryocooler to cool the air to cryogenic temperatures; communicating the cryogenic air through a distillation column to separate the cryogenic air into multiple products, including LOX and one or more byproducts; communicating the separated LOX into a patient portable unit configured to store the LOX and deliver gaseous oxygen (GOX) to a patient, the patient portable unit being portable by the patient; and communicating at least one of the byproducts though the recuperative heat exchanger such that heat is transferred in the recuperative heat exchanger from the purified air to the at least one byproduct from the distillation column.

In accordance with another embodiment of the present disclosure, a system for generating liquid oxygen (LOX) for portable use by a patient includes patient portable means configured to store LOX and deliver gaseous oxygen (GOX) to the patient, and mobile means configured to generate LOX by cryogenic separation of air and deliver the generated LOX to the patient portable means. The mobile means includes pressuring means for receiving and pressurizing air; purifying means for removing impurities from the pressurized air; heat exchanging means for cooling the purified air; cryocooler means for receiving cooled air from the heat exchanging means and further cooling the air to cryogenic temperatures; and distillation means for separating the cryogenic air into multiple products, including LOX and one or more byproducts, communicating the LOX toward storage, communicating at least one byproduct toward the heat exchanging means as at least one cold byproduct flow. The heat exchanging means is configured to cool the purified air by transferring heat from the purified air to the at least one cold byproduct flow.

BRIEF DESCRIPTION OF THE DRAWINGS

Some embodiments of the disclosure may be understood by referring, in part, to the following description and the accompanying drawings wherein.

DETAILED DESCRIPTION OF THE DRAWINGS

Selected embodiments of the disclosure may be understood by reference, in part, to FIGS. 1-9. The present disclosure is broadly concerned with systems and methods for generating liquid oxygen (LOX) for portable use. In some embodiments, a system for generating LOX for portable use by a patient includes a patient portable unit configured to store LOX and deliver gaseous oxygen (GOX) to the patient, and a mobile base unit configured to generate LOX by cryogenic separation of air and deliver the generated LOX to the patient portable unit. The mobile base unit may include a compressor that receives and pressurizes air, one or more filters, a purifier that removes impurities from the pressurized air, a heat exchanger that cools the purified air, a cryocooler that further cools the air to cryogenic temperatures, and a distillation unit that separates the cryogenic air into multiple products, including LOX and one or more cold byproducts. The separated LOX is transferred directly into the patient portable unit or otherwise stored (e.g., in a reservoir of the base unit) for later use. At least one of the cold byproducts from the distillation process is passed back through the heat exchanger to facilitate heat transfer from the incoming purified air to cold byproduct(s) in order to cool the purified air.

Figure 1:
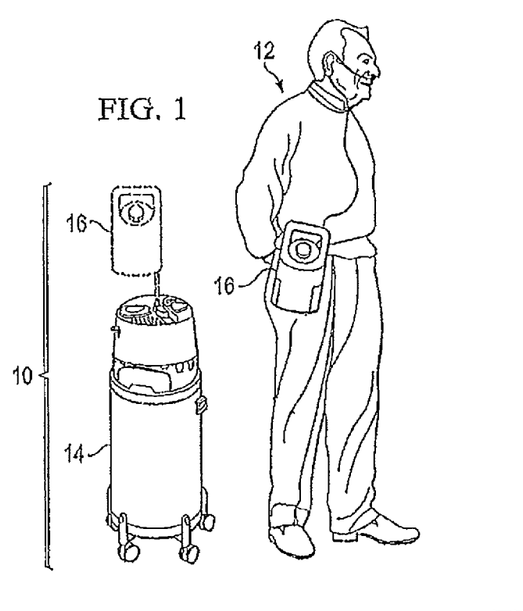
FIG. 1 illustrates an example system for generating and storing oxygen for portable use by a patient, according to certain embodiments of the present disclosure.

FIG. 1 illustrates an example system 10 for generating and storing oxygen for portable use by a patient 12, according to certain embodiments of the present disclosure. System 10 is generally configured to generate liquid oxygen (LOX) from ambient air, and store the generated LOX for portable use by patient 12. In some embodiments, system 10 may include a base unit 14 and a patient portable unit 16. Base unit 14 may be configured to generate LOX from ambient air and transfer generated LOX to patient portable unit 16. In some embodiments, base unit 14 may include a reservoir configured to store generated LOX before transferring to patient portable unit 16. In addition or alternatively, base unit 14 may transfer generated LOX directly to patient portable unit 16, rather than to a reservoir of base unit 16.

Patient portable unit 16 may be generally configured to store LOX received from base unit 14 and supply GOX (converted from the stored LOX) to patient 12 for breathing. Patient portable unit 16 may be portable such that patient 12 may carry unit 16 disconnected from base unit 14. For example, patient portable unit 16 may be similar to a portable LOX unit used in a HELiOS Personal Oxygen System by Puritan Bennett. In some embodiments, patient portable unit 16 may be connected to base unit 14 for filling with LOX, and removed or disconnected from base unit 14 to be carried by patient 12 for portable use.

In some embodiments, base unit 14 is mobile such that base unit 14 may bay be transported, e.g., to a patient's home, between rooms of a patient's home, around a hospital or other care facility, etc. For example, base unit 14 may be on wheels or may have a size and weight that may be carried by a person, e.g., patient 12 or a caretaker. Thus, base unit 14 and patient portable unit 16 may be mobile, but patient portable unit 16 may be smaller and lighter and thus more portable by patient 12 during use.

Base unit 14 and patient portable unit 16 may include any coupling systems or devices configured to detachably couple patient portable unit 16 to base unit 14 for filling patient portable unit 16 with LOX, including any suitable seals or other components configured to prevent leaking.

In some embodiments, base unit 14 may also provide GOX directly to patient 12. For example, as discussed in greater detail below, GOX generated as a byproduct of the LOX generation by system 10 may be provided directly to patient 12 from base unit 14 (or routed though patient portable unit 16 connected to base unit 14).

In other embodiments, base unit 14 and patient portable unit 16 may be integrated into a single portable unit configured to be carried by or otherwise portable with patient 12.

In some embodiments, system 10 may be fully or partially integrated with a ventilator, CPAP device, or other breathing assistance system. For example, system 10 may be integrated with a ventilator and configured to generate LOX and/or GOX. The generated LOX may be stored in a reservoir associated with the ventilator for current or future delivery (as GOX) to the ventilated patient (e.g., as supplemental oxygen delivered along with air) and/or stored in a detachable patient portable unit 16 for future use by the ventilated patient or another patient. In addition, GOX generated as a byproduct of the LOX generation by system 10 may be provided to the ventilated patient (e.g., as supplemental oxygen delivered along with air).

Figure 2:
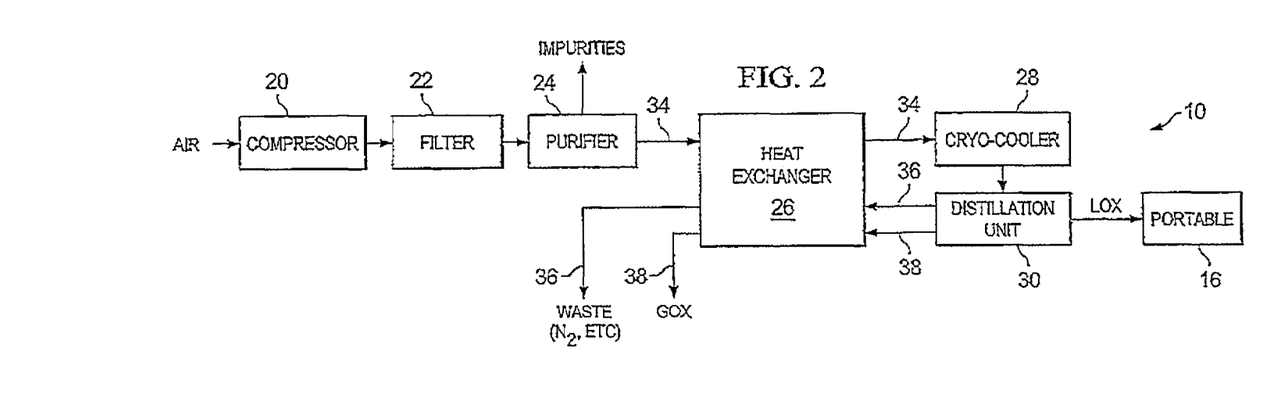
FIG. 2 illustrates an example functional block diagram of the system of FIG. 1, according to certain embodiments of the present disclosure.

FIG. 2 illustrates an example functional block diagram of system 10, according to certain embodiments of the present disclosure. In such embodiments, system 10 includes a compressor 20, a filter 22, a purifier 24, a heat exchanger 26, a cryocooler 28, a distillation unit 30, and patient portable unit 16. Components 20, 22, 24, 26, 28 and 30 may be housed in a base unit 14. As discussed above, patient portable unit 16 may be integrated with, or detachably coupled to, base unit 14.

Compressor 20 may include any device or system configured to compress air in order to increase the pressure of the air. For example, compressor 20 may be configured to compress ambient air from atmospheric pressure to a suitable pressure for cooling and extracting oxygen from the air.

Filter 22 may include any suitable air filter for removing particles from air.

Purifier 24 may include any system suitable for removing impurities having a higher freezing point than the LOX temperature (approximately 90° K), e.g., CO2, water vapor, and/or volatile organic compounds, from the compressed air. Such impurities may condense in the conduits of heat exchanger 26, cryocooler 28, distillation unit 30, and/or other components of system 10, which may be undesirable. Thus, removing such impurities before entering into heat exchanger 26 may be advantageous, e.g., to reduce potential clogging of various fluid conduits in system 10.

Figure 4:
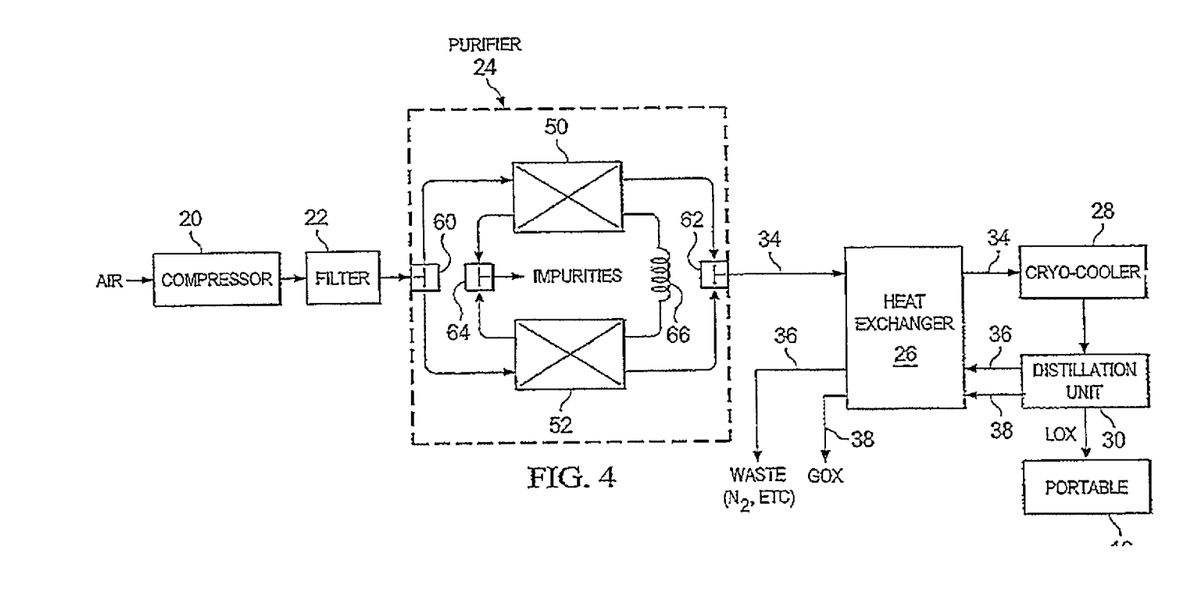
FIGS. 4 and 5 illustrate two example configurations of a purifier for use with certain embodiments of the system of FIG. 1.
Figure 5:
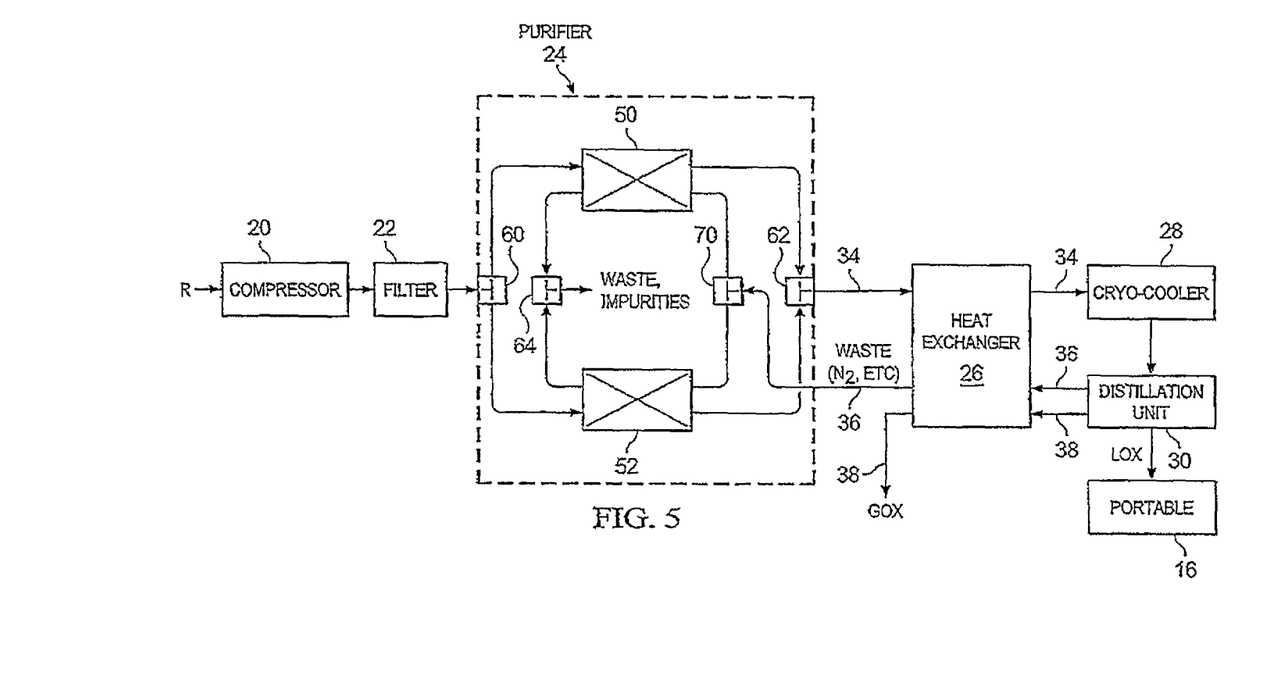

As examples, purifier 24 may include a pressure swing adsorption (PSA), vacuum swing adsorption (VSA), or thermal drying system. In some embodiments, purifier 24 may include a PSA or VSA purifier with two or more columns used in an alternating manner in order to accumulate and then purge impurities, as discussed with reference to FIGS. 4 and 5. FIGS. 4 and 5 provide two example configurations of purifier 24 for use with certain embodiments of system 10, including the embodiments of system 10 shown in FIGS. 2 and 3.

Heat exchanger 26 may include any system or device for transferring heat away from air received from purifier 24 to be delivered to cryocooler 28. Heat exchanger 26 may be a recuperative heat exchanger (e.g., a parallel-flow, cross-flow, or counter-flow heat exchanger) configured to transfer heat from air received from purifier 24 to be delivered to cryocooler 28 (indicated by arrows 34) to one or more cold waste fluids from distillation unit 30, e.g., liquid and/or gaseous N2 and other waste gasses (indicated by arrows 36) and/or liquid and/or gaseous oxygen (indicated by arrows 38).

Figure 6:
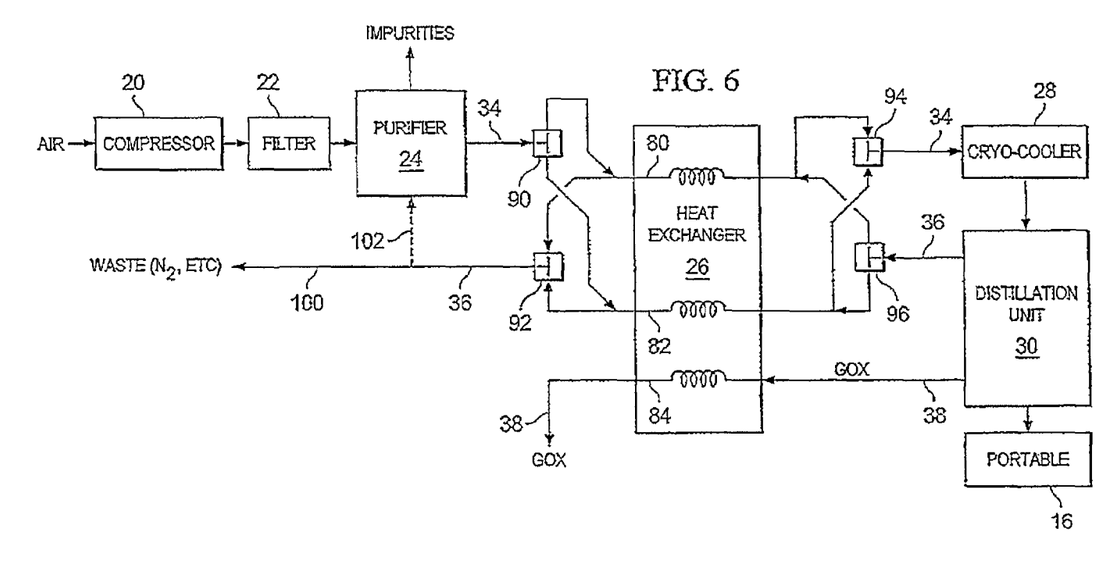
FIGS. 6 and 7 illustrate two example configurations of a heat exchanger for use with certain embodiments of the system of FIG. 1.
Figure 7:
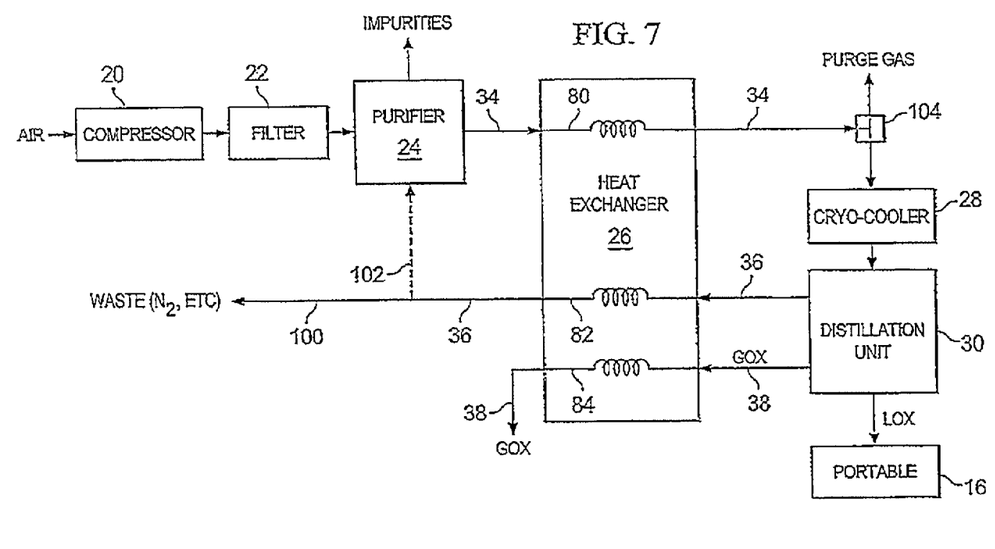

In some embodiments, heat exchanger 26 may also provide further purification of the air received from purifier 24. For example, as shown in FIG. 6, heat exchanger 26 may be a reversing type (regenerative) heat exchanger configured to use multiple flow paths in an alternating manner such that impurities are allowed to freeze on heat transfer surfaces (referred to as thermal purification) in an active flow path, the flow paths are then switched, and the accumulated impurities are then flushed out by a reverse flow through the now-inactive flow path. Such configuration may allow continuous LOX production, as the process need not be interrupted to purge out the heat exchanger conduits. FIGS. 6 and 7 discussed below illustrate two example configurations of heat exchanger 26 for use with certain embodiments of system 10, including the embodiments of system 10 shown in FIGS. 2 and 3.

Cryocooler 28 may include any system or device for cooling the compressed air from heat exchanger 26 to cryogenic temperatures, to at least partially liquify the gasses. For example, cryocooler 28 may cool the air feed to approximately −300° F. or −185° C., to a liquid nitrogen temperature, or to a liquid oxygen temperature. In some embodiments, cryocooler 28 may provide a refrigeration process that includes expansion of one or more elevated pressure process streams to achieve the desired cryogenic temperatures. In some embodiments, cryocooler 28 may comprise a reverse-Brayton cryocooler.

Distillation unit 30 may include any system or device for separating the cryogenic air into components. In the illustrated embodiment, distillation unit 30 may separate the air into three streams: (a) LOX, (b) GOX (or saturated LOX/COX), and (c) waste (e.g., gaseous and/or liquid N2, argon, etc.). As shown in FIG. 2, the LOX may be transferred to a reservoir in base unit 14 and/or to patient portable unit 16. The cold GOX (or saturated LOX/GOX) and waste streams emerging from distillation unit 30 may be rerouted back through heat exchanger 26, as indicated by arrows 36 and 38, to cool the air feed entering heat exchanger 26. The heat exchange between the feed air stream and the product/waste streams from distillation unit 30 may reduce or minimize the net cooling load on system 10, and thus reduce or minimize the energy consumption of system 10.

In some embodiments, distillation unit 30 includes one or more compact cryogenic distillation columns to separate the air into desired products. For example, in some embodiments, as discussed below regarding FIGS. 8 and 9, distillation unit 30 may comprise an enriching section located above a stripping section, with both located between a condenser and an evaporator.

In operation, ambient air enters compressor 20 and is compressed to a desired pressure. The compressed air feed is then passed through one or more filters 22 to remove various impurities or particles. The air feed is then passed through purifier 24, to remove impurities (e.g., CO2, water vapor, and/or volatile organic compounds) from the air so that the impurities are prevented from entering into, and condensing inside, the colder components of system 10, e.g., heat exchanger 26, cryocooler 28, distillation unit 30, etc. In some embodiments in which purifier 24 includes multiple columns, a portion of the air stream passing through an active column may be re-routed back through an inactive column to purge accumulated impurities from the inactive column, as discussed with reference to FIGS. 4 and 5 below.

After passing through purifier 24, the air feed is passed though heat exchanger 26, where the air is cooled by cold byproducts from distillation unit 30 and/or by other coolant(s) passing through heat exchanger 26. In some embodiments, heat exchanger 26 is a reversing type (regenerative) heat exchanger in which the air feed and cold byproducts from distillation unit 30 are passed through flow paths of heat exchanger 26 in opposite directions and in an alternating manner to purge accumulated impurities within such flow paths, e.g., as discussed below regarding FIG. 7.

After passing through heat exchanger 26, the cooled air is passed to cryocooler 28, which further cools the air to cryogenic temperatures, which at least partially liquifies the air. The cryogenic air is then passed to distillation unit 30, which separates the cryogenic air into various components, e.g., LOX, GOX (or saturated LOX/GOX), and waste product (e.g., gaseous and/or liquid N2, argon, etc.). The LOX may be transferred to a reservoir in base unit 14 and/or to patient portable unit 16. The cold GOX (or saturated LOX/GOX) and waste streams emerging from distillation unit 30 may be rerouted back through heat exchanger 26, as indicated by arrows 36 and 38, to cool the air feed entering heat exchanger 26. In addition, in some embodiments or applications of system 10, the GOX may be delivered to patient 12 or stored for future use by patient 12.

In some embodiments, system 10 includes a control system configured to monitor and control the operation of system 10. For example, the control system may monitor the processes and states of system 10 at various locations using pressures, temperatures, flow rates, liquid level, liquid weight, oxygen concentration, impurity levels, etc. The control system may also include various valves to control and/or channel the various flows within system 10. The control system may also include various pressure safety devices and electrical safety devices.

Figure 3:
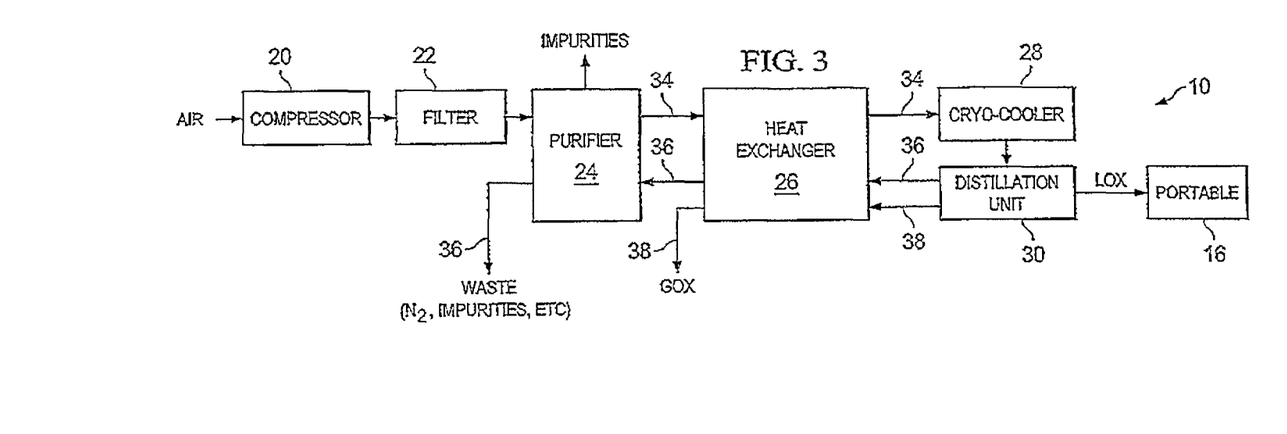
FIG. 3 illustrates another example functional block diagram of the system of FIG. 1, according to another embodiment of the present disclosure.

FIG. 3 illustrates another example functional block diagram of system 10, according to another embodiment of the present disclosure. In this embodiment, unlike that of FIG. 2, waste stream 36 from distillation unit 30 and passing through heat exchanger 26 is further routed through purifier 24 for purging accumulated impurities from columns of purifier 24. This process is shown and discussed in greater detail below with reference to FIG. 5.

FIGS. 4 and 5 illustrate functional block diagrams of two example configurations of purifier 24 for use with certain embodiments of system 10, including the embodiments of system 10 shown in FIGS. 2 and 3. In the embodiments shown in FIGS. 4 and 5, purifier 24 is a pressure swing adsorption (PSA), vacuum swing adsorption (VSA), or other type of purifier that includes two columns 50 and 52 used in an alternating manner in order to accumulate and then purge impurities. Purifier 24 may also include various valves configured to control the alternating use of columns 50 and 52, as discussed below. In general, purifier 24 as shown in FIGS. 4 and 5 are similar. However, as discussed below, purifier 24 shown in FIG. 4 uses a fraction of the air stream passing through an active column 50 (52) to purge impurities from the other, inactive column 52 (50), while purifier 24 shown in FIG. 5 uses a waste product stream 36 from distillation unit 30 to purge impurities from the inactive column 50 (52).

In the embodiment shown in FIG. 4, purifier 24 includes three valves 60, 62, and 64, and a flow regulator 66. Valves 60, 62, and 64 may be any suitable types of valves. For example, valves 60, 62, and 64 may be three-way solenoid valves. Flow regulator 66 may comprise any device configured to regulate flow through a conduit connecting columns 50 and 52, e.g., a suitably-sized orifice, capillary tube(s), or one or more valves).

In operation, valves 60, 62, and 64 may cooperate to alternate columns 50 and 52 between active and inactive—when column 50 is active (i.e., allowing the air feed to pass through for purification), column 52 is inactive, and vice versa. As air passes through the active column, impurities are collected (e.g., adsorbed) in the column. A fraction (e.g., 20%-30%) of the purified air exiting the active column is re-routed backwards through the inactive column in order to purge impurities that were collected in the inactive column when the inactive column was operating as the active column.

In operation, valve 60 receives the air feed from filter 22 and directs the air to the active column, say column 50. The air passes through and is filtered by active column 50. A majority of the purified air exiting column 50 is passed to valve 62, which is set to pass the purified air along to heat exchanger 26, along path 34. A smaller fraction of the purified air exiting column 50 is routed back through inactive column 52 via purge gas flow device 66, passes through inactive column 52 and purges impurities collected in inactive column 52 (during a previous active period of column 52). Purge gas flow device 66 may comprise any system or device for controlling the fraction of gas exiting active column 50 that is re-routed for purging inactive column 52, e.g., a suitably-sized orifice, capillary tube(s), or one or more valves. The fraction of air routed back through inactive column 52 passes through valve 64, which is set to allow passage from column 52, and out of purifier 24.

After some period of time (e.g., 30 seconds), valves 60, 62, and 64 are controlled to switch column 52 to the active column and column 50 to the inactive column. Thus, the air feed from filter 22 passes through valve 60 and through active column 62. A larger fraction of the purified air exiting column 52 is passed to valve 62, which is now set to pass the purified air along to heat exchanger 26, along path 34. A smaller fraction of the purified air exiting column 52 is routed back through inactive column 50 via purge gas flow device 66, passes through inactive column 50 and purges impurities collected in inactive column 50 (during the previous active period of column 50). The fraction of air routed back through inactive column 50 passes through valve 64, which is now set to allow passage from column 50, and out of purifier 24.

In the embodiment shown in FIG. 5, waste product stream 36 from distillation unit 30, rather than a fraction of the air exiting the active column 50 or 52, is used to purge impurities from the inactive column 50 or 52. For instance, purifier 24 may include valves 60, 62, and 64 similar to purifier 24 of FIG. 4, but may also include a line in and another valve 70 configured to deliver waste stream 36 back through the inactive column 50 or 52 to purge that column. Valve 70 may be any suitable type of valves, e.g., a three-way solenoid valve. Thus, all of the air passing through the active column may be delivered to heat exchanger 26, as opposed to the embodiment shown in FIG. 4.

FIGS. 6 and 7 discussed below illustrate two example configurations of heat exchanger 26 for use with certain embodiments of system 10, including the embodiments of system 10 shown in FIGS. 2-5. Thus, any combination of purifiers 24 shown in FIGS. 4 and 5 and heat exchanger 26 shown in FIGS. 6 and 7 may be used with either embodiment of system 10 shown in FIGS. 2-3.

Heat exchanger 26 shown in FIG. 6 is a reversing type (regenerative) heat exchanger configured to use multiple flow paths, or conduits, in an alternating manner in order to flush out accumulated impurities on heat transfer surfaces of the flow paths of heat exchanger 26. For example, heat exchanger 26 may include conduits 80, 82, and 84, and valves 90, 92, 94, and 96. Valves 90, 92, 94, and 96 may be any suitable types of valves. For example, valves 90, 92, 94, and 96 may be three-way solenoid valves.

In operation, valves 90, 92, 94, and 96 may cooperate to alternate the flow of purified air stream 34 and the flow of waste stream 36 between conduits 80 and 82. For example, in a first state in which conduit 80 is the active conduit and conduit 82 is the inactive conduit, valves 90 and 94 are set such that air stream 34 is directed from purifier 24, through valve 90, through active conduit 80, through valve 94, and toward cryocooler 28. In this first state, valves 92 and 96 are set such that waste stream 36 is directed from distillation unit 30 and through valve 96, through inactive conduit 82, and through valve 92. Waste stream may then be directed out of system 10, as indicated by arrow 100 (e.g., according to the embodiment shown in FIG. 4), or back through purifier 24 for purging the inactive column of purifier 24, as indicated by arrow 102 (e.g., according to the embodiment shown in FIG. 5).

After some time operating in this first state (e.g., 30 seconds), heat exchanger 26 may switch to a second state in which conduit 82 is the active conduit and conduit 80 is the inactive conduit. Valves 90 and 94 are set such that air stream 34 is directed from purifier 24, through valve 90, through active conduit 82, through valve 94, and toward cryocooler 28. Valves 92 and 96 are set such that waste stream 36 is directed from distillation unit 30 and through valve 96, through inactive conduit 80, and through valve 92. Waste stream may then be directed out of system 10, as indicated by arrow 100 (e.g., according to the embodiment shown in FIG. 4), or back through purifier 24 for purging the inactive column of purifier 24, as indicated by arrow 102 (e.g., according to the embodiment shown in FIG. 5).

In this manner, heat exchanger 26 may switch back and forth between passing streams 34 and 36 through conduits 80 and 82. Passing waste stream 36 through the inactive conduit 80 or 82 may purge accumulated (e.g., frozen or condensed) impurities in the inactive conduit 80 or 82, which may further increase the purification of air passing through system 10. Such configuration may allow continuous LOX production, as the process need not be interrupted to purge out the conduits of heat exchanger 26. In some embodiments, GOX may be passed through conduit 84 for promoting heat transfer in heat exchanger 26. In other embodiments, GOX may not be passed through heat exchanger 26.

Heat exchanger 26 shown in FIG. 7 is a non-reversing type heat exchanger, which may include conduits 80, 82, and 84 for communicating air stream 34, waste stream 36, and GOX stream 38, respectively. After passing through heat exchanger 26, waste stream may be directed out of system 10, as indicated by arrow 100 (e.g., according to the embodiment shown in FIG. 4), or back through purifier 24 for purging the inactive column of purifier 24, as indicated by arrow 102 (e.g., according to the embodiment shown in FIG. 5). In some embodiments, a purge valve 104 may be provided between heat exchanger 26 and cryocooler 28 to purge gas from the air stream 34.

Figure 8:
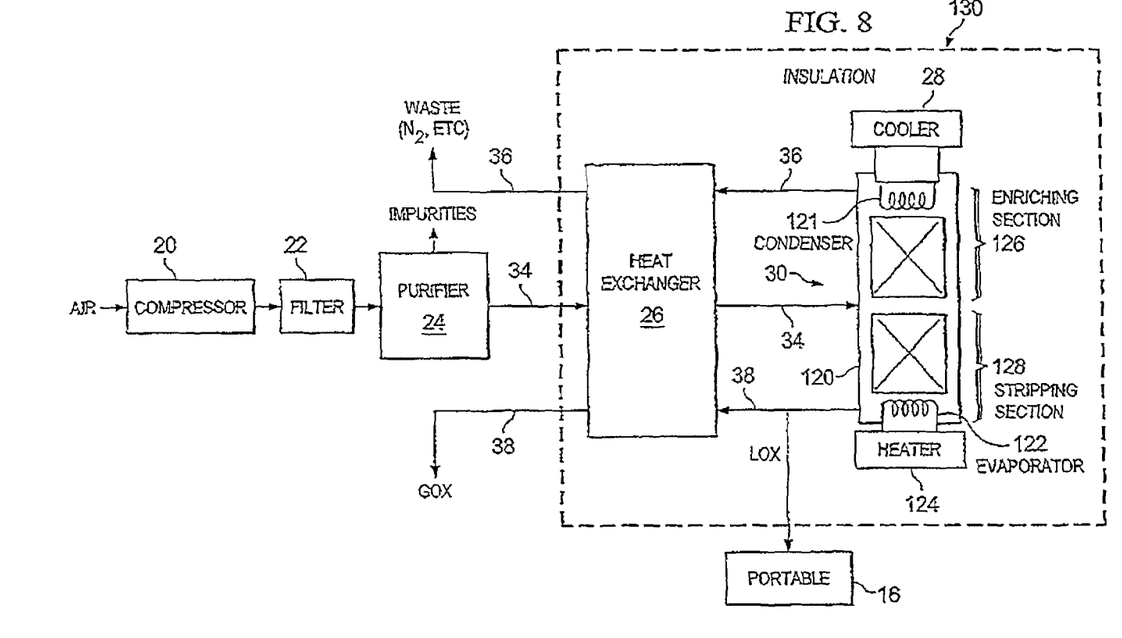
FIGS. 8 and 9 illustrate two example configurations of a distillation unit for use with certain embodiments of the system of FIG. 1.

FIG. 8 illustrates details of an example distillation unit 30, according to certain embodiments of the present disclosure. The disclosed distillation unit 30 may be used in connection with any of the embodiments discussed above, e.g., in connection with any combination of purifier 24 and heat exchanger 26 configuration.

As discussed above regarding FIG. 2, distillation unit 30 may include any system or device for separating the cryogenic air into multiple products. For example, distillation unit 30 may comprise a rectification unit, a distillation column, or a packed bed unit. In some embodiments, distillation unit 30 includes a compact cryogenic distillation column 120 operable to separate the air into the following products: (a) LOX, (b) GOX (or saturated LOX/GOX), and (c) waste (e.g., gaseous and/or liquid N2, argon, etc.). As shown in FIG. 8, the LOX may be transferred to patient portable unit 16 (or in other embodiments, to a reservoir in base unit 14). The cold GOX (or saturated LOX/GOX) and waste streams emerging from distillation unit 30 may be rerouted back through heat exchanger 26, as indicated by arrows 36 and 38, to cool the air feed entering heat exchanger 26.

In the example illustrated embodiment, distillation column 120 comprises an HIDiC (heat integrated distillation column), wherein the heat of the enriching section is transferred to the stripping section. In the conventional distillation system, heat efficiency is comparatively low, because the waste heat at the top of the enriching section is not put to use. By contrast, the HIDiC column makes use of this heat, by promoting heat transfer from the enriching section to the stripping section. Pressure may be applied to the vapor, compressing it and causing the temperature to rise, and the resultant heat may be transferred to the stripping section, which may be achieved through HIDiC's distinctive longitudinal partitioning of the distillation column into enriching and stripping sections.

In the illustrated embodiment, distillation column 120 includes a condenser 121 at a top side that is coupled to a cryocooler (which is referred to herein as cryocooler 28, but in some embodiments may be a separate cryocooler), an evaporator 122 coupled to a heater 124 at the bottom side, an enriching section 126, and a stripping section 128. In general, within distillation column 120, at least a portion of the cold fluid travels down from condenser 120 toward heater 124, where it is evaporated by evaporator 122. At least a portion of the warmed gas then travels back upwards toward cryocooler 28, where it is condensed by condenser 121. Thus, in this embodiment, cryocooler 28 provides the reflux needed for the process.

In particular embodiments, vapor from stripping section 128 may be fed to enriching section 126 only after compression has elevated its temperature. The liquid from the bottom of enriching section 126 is thus at a higher pressure, so the pressure needs to be reduced before the liquid enters the top of stripping section 128. Heat from individual trays in enriching section 126 is conducted directly to corresponding trays in stripping section 128, through section walls. The vapor rate in enriching section 126 decreases progressively as the vapor approaches the top. Conversely, the liquid rate in enriching section 126 increases progressively as the liquid approaches the bottom of the section.

In the illustrated embodiment, waste gasses (e.g., N2) are removed from column 120 near condenser 121, while LOX and GOX are removed near evaporator 122. As discussed above, the LOX removed from column 120 may be transferred to patient portable unit 16 (or in other embodiments, to a reservoir in base unit 14), while the cold GOX (or saturated LOX/GOX) and waste gasses from column 120 may be rerouted back through heat exchanger 26.

The air feed 34 from heat exchanger 26 may be delivered to cryocooler 28 and/or distillation unit 30 at any suitable location(s). For example, air stream 34 from heat exchanger 26 may be delivered directly to cryocooler 28. As another example, air stream 34 may be delivered to distillation unit 30 (e.g., at a location between enriching section 126 and stripping section 128) and then travel toward cryocooler 28. In other embodiments, multiple cryocoolers may be provided at different locations of system 10.

Attaching cryocooler 28 directly to the condenser 121 of the distillation column 120 may provide the thermal properties required for separating the air using a relatively small distillation column 120. For example, distillation column 120 may be approximately 2 feet tall.

The portions of the cryogenic air separation process that operate at very low temperatures, e.g., distillation column 120, heat exchanger 26, and cold interconnecting piping, are well insulated. For example, such components may be housed within an insulation unit 130, as shown in FIG. 8. Insulation unit 130 may comprise any suitable type(s) of insulation known in the art, e.g., vacuum insulation, multilayer insulation (MLI), and/or thermal insulation. As another example, insulation unit 130 may be packed with rock wool, perlite, or other suitable material to provide insulation and minimize convection currents.

Figure 9:
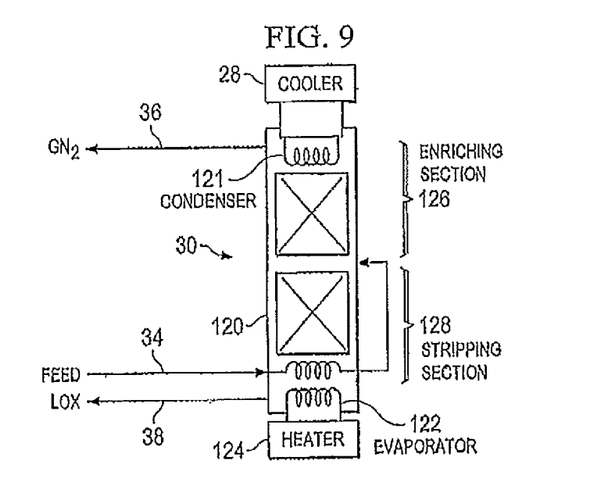

FIG. 9 illustrates another example configuration of distillation unit 30, according to certain other embodiments of the present disclosure. The disclosed distillation unit 30 of FIG. 9 may be used in connection with any of the embodiments discussed above, e.g., in connection with any combination of purifier 24 and heat exchanger 26 configuration.

In this embodiment, the air feed 34 from heat exchanger 26 passes through distillation column 120 at a bottom portion of column 120, near heater 124, and is then routed back into column 120 at a middle portion between enriching section 126 and stripping section 128. This configuration may provide beneficial heat transfer and/or separation results.

It will be appreciated that while the disclosure is particularly described in the context of breathing assistance systems, the apparatuses, techniques, and methods disclosed herein may be similarly applied in other contexts. Additionally, it should be understood that various changes, substitutions and alterations can be made herein without departing from the spirit and scope of the disclosure as illustrated by the following claims.

What is claimed is:

1. A system comprising:
    a patient portable unit configured to store LOX and deliver gaseous oxygen (GOX) to a patient, the patient portable unit being configured to be attached to an article worn by the patient, the patient portable unit configured to convert stored LOX into GOX for delivery to a patient, the patient portable unit being defined by a first housing and wherein the patient portable unit includes a reservoir that stores LOX or GOX;
    a mobile base unit that generates LOX by cryogenic separation of air and delivers the generated LOX to the patient portable unit, wherein the mobile base unit transfers all the generated LOX directly to the patient portable unit, rather than to a reservoir of the mobile base unit, the patient portable unit being smaller and lighter than the mobile base unit, the patient portable unit configured to be disconnected from the mobile base unit when the patient is mobile and the GOX is being delivered to the patient, the patient portable unit configured to convert the LOX received from the mobile base unit to GOX, the patient portable unit configured to deliver the GOX converted from LOX in the patient portable unit, the mobile base unit being defined by a second housing removably attached to the first housing, the mobile base unit defining a flow pathway including:
        a compressor configured to receive the air and pressurize the air;
        a purifier configured to remove impurities from the pressurized air by passing pressurized air through a multiple column purifier, the impurities including volatile organic compounds;
        a recuperative heat exchanger configured to cool the purified air, the recuperative heat exchanger being entirely downstream of the purifier in the flow pathway such that all of the air from the purifier is passed to the recuperative heat exchanger;
        a cryocooler configured to receive cooled air from the recuperative heat exchanger and further cool the air to cryogenic temperatures; and
        a distillation unit configured to:
            separate the cryogenic air into multiple products, including LOX and one or more byproducts;
            communicate the LOX toward storage; and
            communicate at least one byproduct toward the recuperative heat exchanger as at least one cold byproduct flow; and
        wherein the recuperative heat exchanger is configured to cool the purified air by transferring heat from the purified air to the at least one cold byproduct flow;
        a conduit that removably connects the patient portable unit to the mobile base unit, the conduit having a seal to prevent leaking at a connection between the patient portable unit to the mobile base unit.

2. The system according to claim 1, wherein the purifier includes multiple columns using in an alternating manner.

3. The system according to claim 1, wherein
    the distillation unit includes a distillation column having a condenser located at a top end of the distillation column; and
    the cryocooler is coupled directly to the condenser located at a top end of the distillation column.

4. The system according to claim 1, wherein:
    the distillation unit is configured to:
        separate the cryogenic air into LOX and byproducts including GOX and waste product, the waste product including N2;
        communicate the waste product toward the recuperative heat exchanger as a waste byproduct flow; and
    the recuperative heat exchanger is configured to cool the purified air by transferring heat from the purified air to the waste byproduct flow.

5. The system according to claim 1, wherein:
    the distillation unit is configured to:
        separate the cryogenic air into LOX and byproducts including GOX and waste product, the waste product including N2;
        communicate the GOX toward the recuperative heat exchanger as a GOX byproduct flow;
        communicate the waste product toward the recuperative heat exchanger as a waste byproduct flow; and
    the recuperative heat exchanger is configured to cool the purified air by transferring heat from the purified air to the GOX byproduct flow and to the waste byproduct flow.

6. The system according to claim 1, wherein the distillation unit is configured to communicate the LOX into the patient portable unit for storage.

7. The system according to claim 1, wherein the distillation unit comprises a heat integrated distillation column (HIDiC) including an enriching section positioned above a stripping section.

8. The system according to claim 1, wherein the recuperative heat exchanger comprises a reversing type heat exchanger including multiple conduits used in an alternating manner to flush condensables or the impurities from the conduits.

* * * * *